United States Patent
Saitoh et al.

(10) Patent No.: US 10,031,101 B2
(45) Date of Patent: Jul. 24, 2018

(54) CHEMICAL/PHYSICAL PHENOMENON DETECTING DEVICE AND METHOD OF PRODUCING THE SAME

(71) Applicants: Sharp Kabushiki Kaisha, Osaka-shi, Osaka (JP); National University Corporation Toyohashi University of Technology, Toyohashi-shi, Aichi (JP)

(72) Inventors: Satoshi Saitoh, Osaka (JP); Toshio Yoshida, Osaka (JP); Tomohiro Konishi, Osaka (JP); Kazuaki Sawada, Toyohashi (JP)

(73) Assignees: SHARP KABUSHIKI KAISHA, Sakai (JP); NATIONAL UNIVERSITY CORP TOYOHASHI UNIVERSITY, Aichi (JP)

( * ) Notice: Subject to any disclaimer, the term of this patent is extended or adjusted under 35 U.S.C. 154(b) by 223 days.

(21) Appl. No.: 14/885,240

(22) Filed: Oct. 16, 2015

(65) Prior Publication Data

US 2016/0109404 A1    Apr. 21, 2016

(30) Foreign Application Priority Data

Oct. 20, 2014 (JP) ................. 2014-214040

(51) Int. Cl.
*G01N 27/414* (2006.01)
(52) U.S. Cl.
CPC ................. *G01N 27/4145* (2013.01)
(58) Field of Classification Search
CPC ................................ G01N 27/4145
See application file for complete search history.

(56) References Cited

U.S. PATENT DOCUMENTS

| 6,255,678 B1 | 7/2001 | Sawada et al. | |
| 6,351,003 B1* | 2/2002 | Kuriyama | H01L 27/14609 257/229 |
| 2005/0062093 A1 | 3/2005 | Sawada et al. | |
| 2006/0129332 A1* | 6/2006 | Mimura | G01N 27/4148 702/23 |
| 2008/0231253 A1* | 9/2008 | Sawada | G01N 27/4148 324/71.1 |
| 2011/0272746 A1 | 11/2011 | Suzuki | |
| 2012/0002201 A1 | 1/2012 | Sawada et al. | |

FOREIGN PATENT DOCUMENTS

| JP | 2002-9274 A | 1/2002 |
| JP | 2002-98667 A | 4/2002 |
| JP | 2006-284225 A | 10/2006 |
| JP | 2007-278760 A | 10/2007 |
| JP | 4195859 B2 | 12/2008 |
| JP | 4231560 B2 | 3/2009 |
| JP | 2011-171575 A | 9/2011 |
| JP | 2011-238751 A | 11/2011 |
| WO | 2010/106800 A1 | 9/2010 |
| WO | 2012/077330 A1 | 6/2012 |

* cited by examiner

*Primary Examiner* — Jermele M Hollington
*Assistant Examiner* — Feba Pothen
(74) *Attorney, Agent, or Firm* — Keating & Bennett, LLP

(57) ABSTRACT

An ion sensor is configured such that part of a P well on which part a sensing section is provided is different, in dopant concentration, from the other part of the P well so that electric charges are injected merely to the sensing section in a state where a voltage is applied to an N-type substrate.

4 Claims, 10 Drawing Sheets

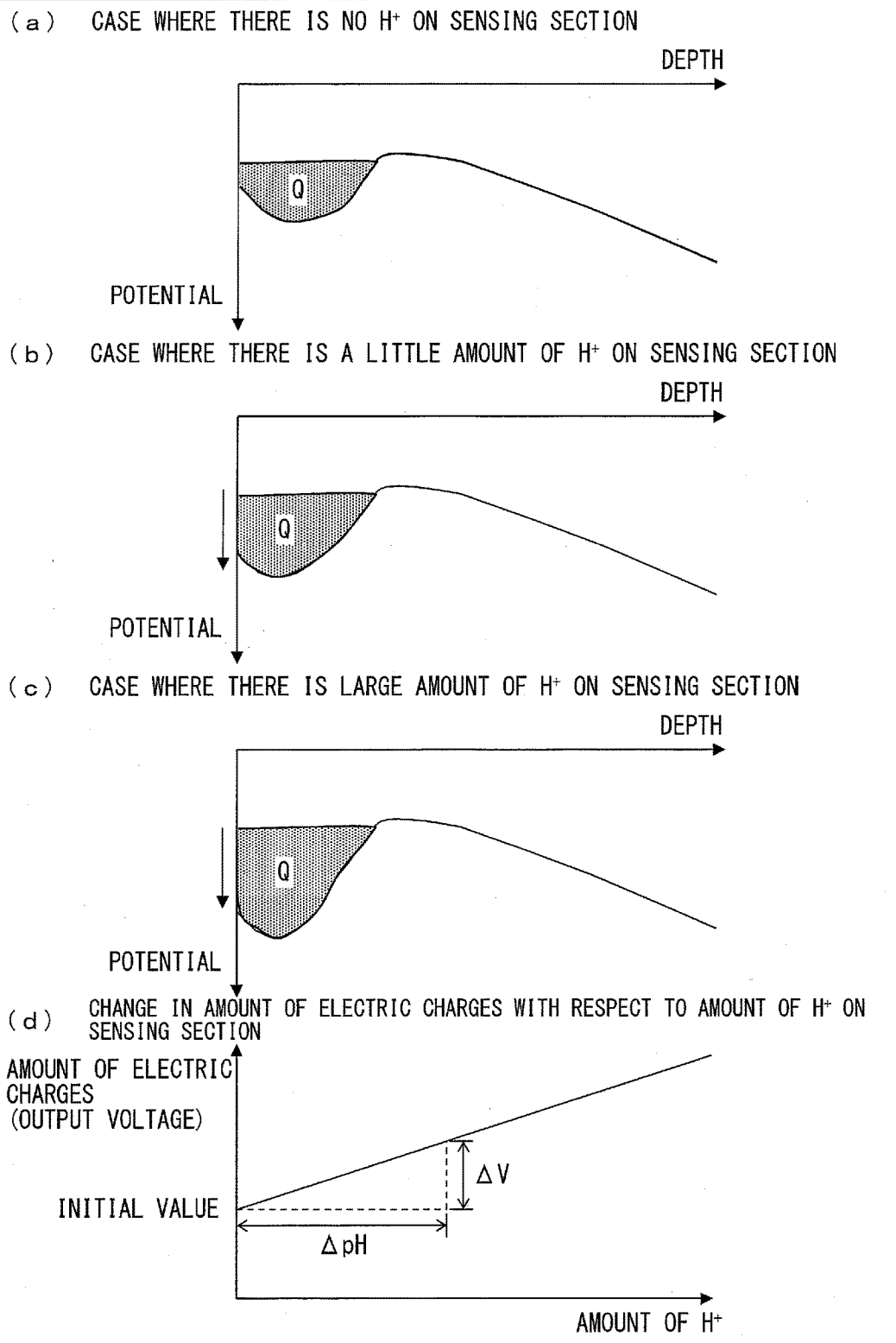

CHEMICAL/PHYSICAL PHENOMENON DETECTING DEVICE AND METHOD OF PRODUCING THE SAME

Figure 1:
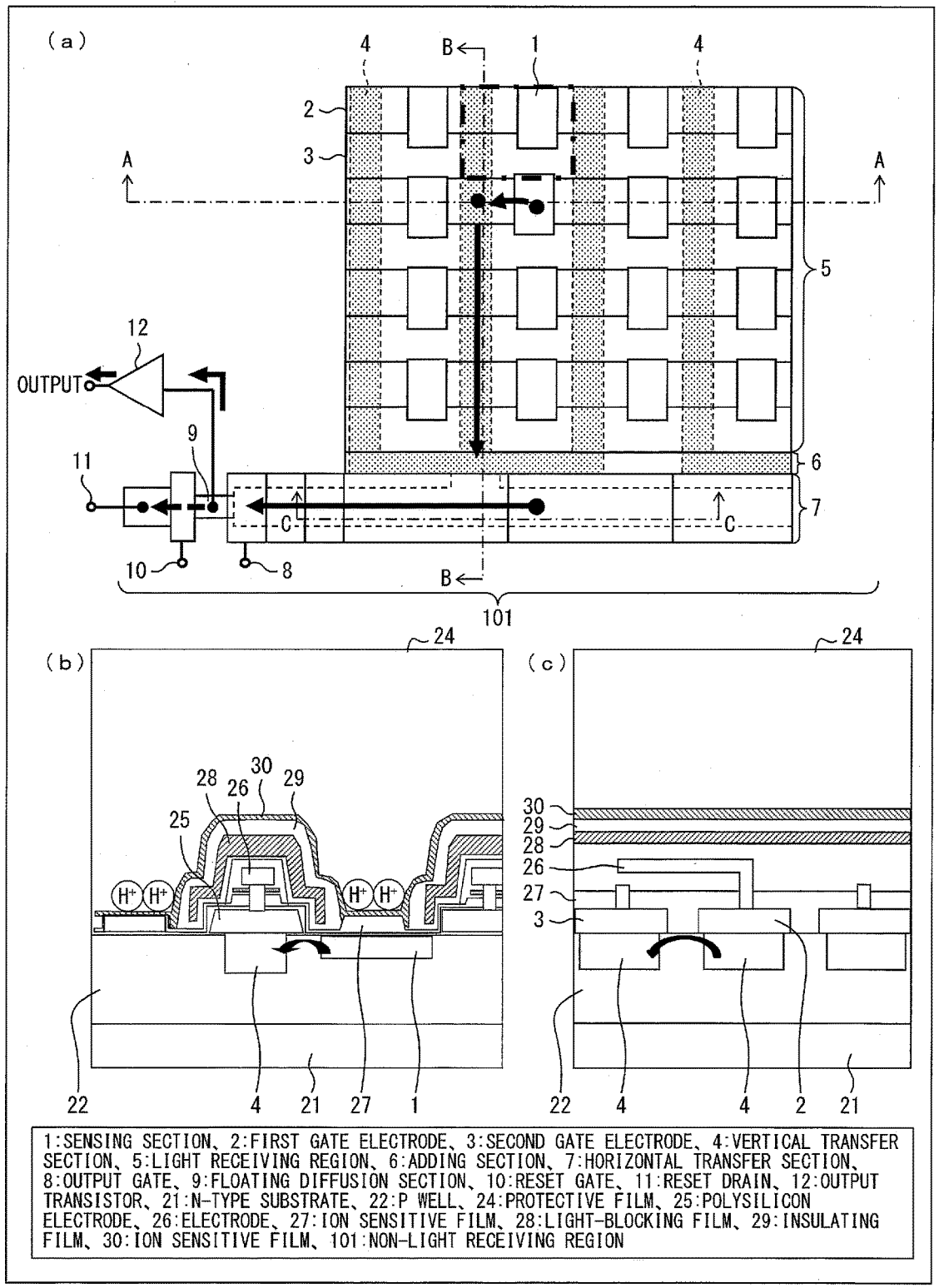

This Nonprovisional application claims priority under 35 U.S.C. § 119 on Patent Application No. 2014-214040 filed in Japan on Oct. 20, 2014, the entire contents of which are hereby incorporated by reference.

TECHNICAL FIELD

The present invention relates to a photodiode-type ion concentration sensor for detecting an ion concentration by detecting an amount of a change in electric potential level of a channel which change is based on a change in electric potential of a surface of a sensing section that is sensitive to an ion, the ion concentration sensor detecting the ion concentration with use of a structure, a production method, a driving method, and the like of a solid-state image sensing device. The present invention further relates to a method of detecting an ion concentration with use of the ion concentration sensor.

BACKGROUND ART

The conventional ion concentration sensors (for example, ion sensitive FETs (ISFET: Ion Sensitive Field Effect Transistor) for detecting a hydrogen ion concentration) have problems of low sensitivity, temporally varied outputs, and the like. As a solution for such problems, a structure has been suggested which detects an amount of a change in electric potential level of a channel which change is based on a change in electric potential level of a surface of a sensing section. The structure requires elements such as an input transistor, an output transistor, and a reset transistor. Therefore, it is difficult to form a fine cell having a size of not more than 10 μm.

The structure has those transistors in each cell. Therefore, not only the sensing section but also a variation in characteristic between such elements in the each cell acutely affects accuracy of readout electric charge. This ultimately causes a great variation in accuracy of the readout electric charge between cells, thereby bringing a problem such that the accuracy is not improved. In view of this, in order to fix a measured value, it is necessary to (i) measure the characteristic of each cell in advance, (ii) create a standard curve in accordance with a result of such measurement, (iii) store data on the standard curve, and (iv) check measurement data with such stored data. This takes a lot of time and labor.

For example, a sensor disclosed in Patent Literature 1 includes an input diode which supplies electric charge, an output gate, and a reset diode. Meanwhile, a sensor disclosed in Patent Literature 2 includes an input diode, an output gate, and a reset section. A sensor disclosed in Patent Literature 3 includes an input diode, an output transistor, and a reset diode. Each of the sensors disclosed in Patent Literatures 1 through 3 is thus arranged such that such elements are provided with respect to one sensing section. Therefore, each of the sensors disclosed in Patent Literatures 1 through 3 has a problem as described above.

In order to solve such problem, Patent Literature 4 discloses a structure similar to an interline CCD (Charge Coupled Device), which is configured such that an electric charge transfer section transfers capacitive electric charge and a section in a vicinity of a sensor converts the capacitive electric charge to a voltage. According to the structure, it is not necessary to provide a reset transistor and an output transistor in each cell. However, the structure still needs an electric charge injection section such as an electrode and a non-sensitive membrane.

CITATION LIST

Patent Literature

[Patent Literature 1]
 Japanese Patent, No. 4195859 (Issue Date: Dec. 17, 2008)
[Patent Literature 2]
 Japanese Patent Application Publication, Tokukai, No. 2002-98667 A (Publication Date: Apr. 5, 2002)
[Patent Literature 3]
 Japanese Patent Application Publication, Tokukai, No. 2007-278760 A (Publication Date: Oct. 25, 2007)
[Patent Literature 4]
 Japanese Patent, No. 4231560 (Issue Date: Mar. 4, 2009)

SUMMARY OF INVENTION

Technical Problem

According to an ion sensor which has highly-integrated and fine cells each having a size of 10 μm, since the cells are fine, each of sensing sections is decreased in area in a case where a transistor, necessary for the each of the cells, accounts for a large part of the each of the cell. Therefore, the ion sensor has problems of low sensitivity and low accuracy.

The present invention has been made in view of the above problems, and an object of the present invention is to increase an area of a sensing section provided in an ion concentration sensor.

Solution to Problem

In order to attain the above object, an ion concentration sensor in accordance with an embodiment of the present invention is an ion concentration sensor including: a semiconductor substrate; a sensing section in which electric charges, used to detect an ion concentration, is accumulated; an electric charge transfer section which transfers the electric charges accumulated in the sensing section; an electric charge detecting section which detects an amount of the electric charges that have been transferred; and an ion sensitive film which changes, depending on the ion concentration, the amount of the electric charges to be accumulated in the sensing section, the sensing section, the electric charge transfer section, and the electric charge detecting section being provided on a diffusion region, on the semiconductor substrate, whose type is opposite to that of the semiconductor substrate, part of the diffusion region on which part the sensing section is provided being different, in dopant concentration, from the other part of the diffusion region so that the electric charges are injected merely to the sensing section in a state where a voltage is applied to the semiconductor substrate.

In order to attain the above object, an ion concentration sensor in accordance with another embodiment of the present invention is an ion concentration sensor including: a sensing section in which electric charges, used to detect an ion concentration of a test body, is accumulated; an electric charge transfer section which transfers the electric charges accumulated in the sensing section; an electric charge detecting section which detects an amount of the electric charges that have been transferred; and an ion sensitive film which changes, depending on the ion concentration, the amount of the electric charges to be accumulated in the sensing section, the sensing section generating the electric charges by photoelectric conversion.

Advantageous Effects of Invention

According to an embodiment or another embodiment of the present invention, it is possible to improve sensitivity and accuracy of an ion concentration sensor by increasing an area of a sensing section provided in the ion concentration sensor.

BRIEF DESCRIPTION OF DRAWINGS (a) of FIG. 1 is an enlarged plan view illustrating part of an ion sensor in accordance with Embodiments 1 through 4 of the present invention. (b) of FIG. 1 is a cross-sectional view illustrating the ion sensor taken along a line A-A illustrated in (a) of FIG. 1 and viewed in a direction of arrows shown by the line A-A. (c) of FIG. 1 is a cross-sectional view illustrating the ion sensor taken along a line B-B or a line C-C illustrated in (a) of FIG. 1 and viewed in a direction of arrows shown by the line B-B or the line C-C.

Figure 2:
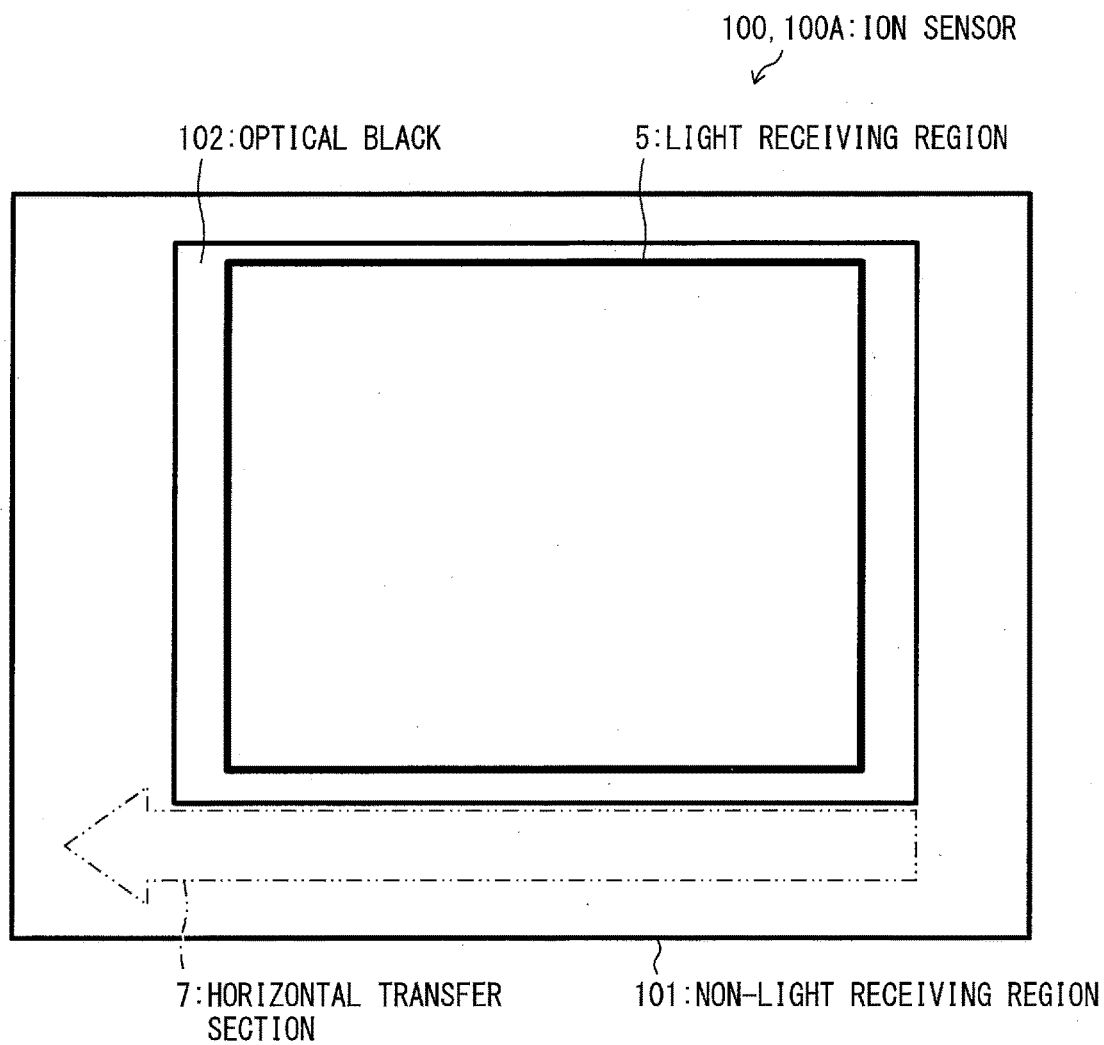

FIG. 2 is a plan view illustrating a configuration of the ion sensor in accordance with Embodiments 1 and 2 of present invention.

Figure 3:
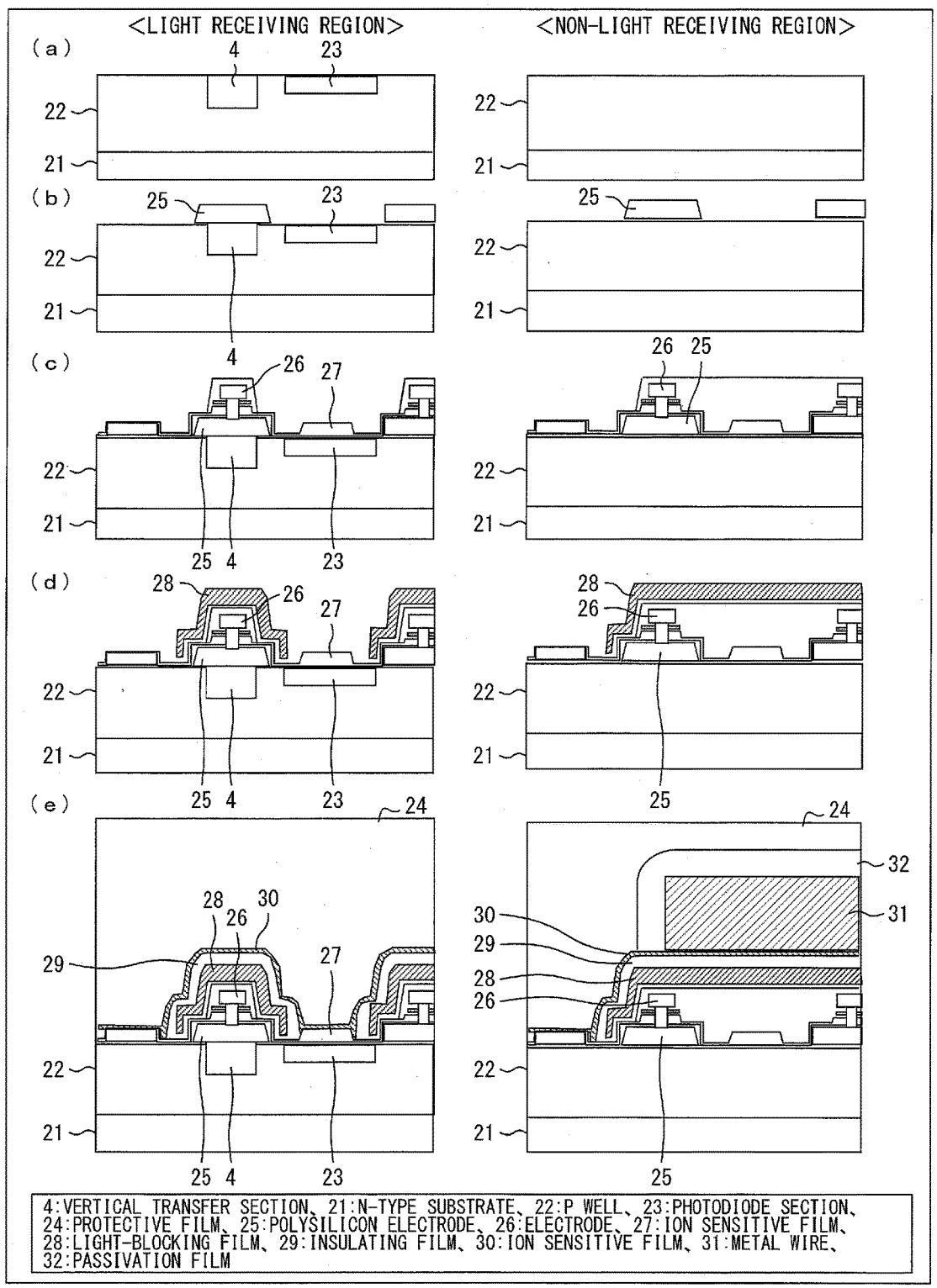

(a) through (e) of FIG. 3 are cross-sectional views each illustrating steps for producing the ion sensor in accordance with Embodiment 1 of the present invention.

Figure 4:
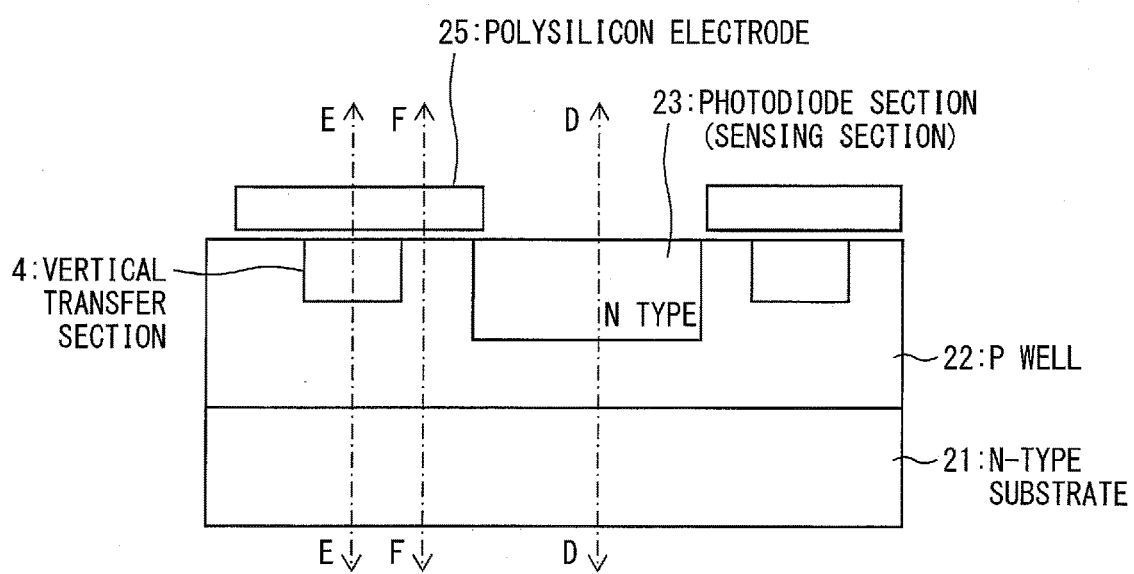

FIG. 4 is a cross-sectional view illustrating a structure of one cell provided in the ion sensor in accordance with Embodiments 1 and 2 of the present invention.

Figure 5:
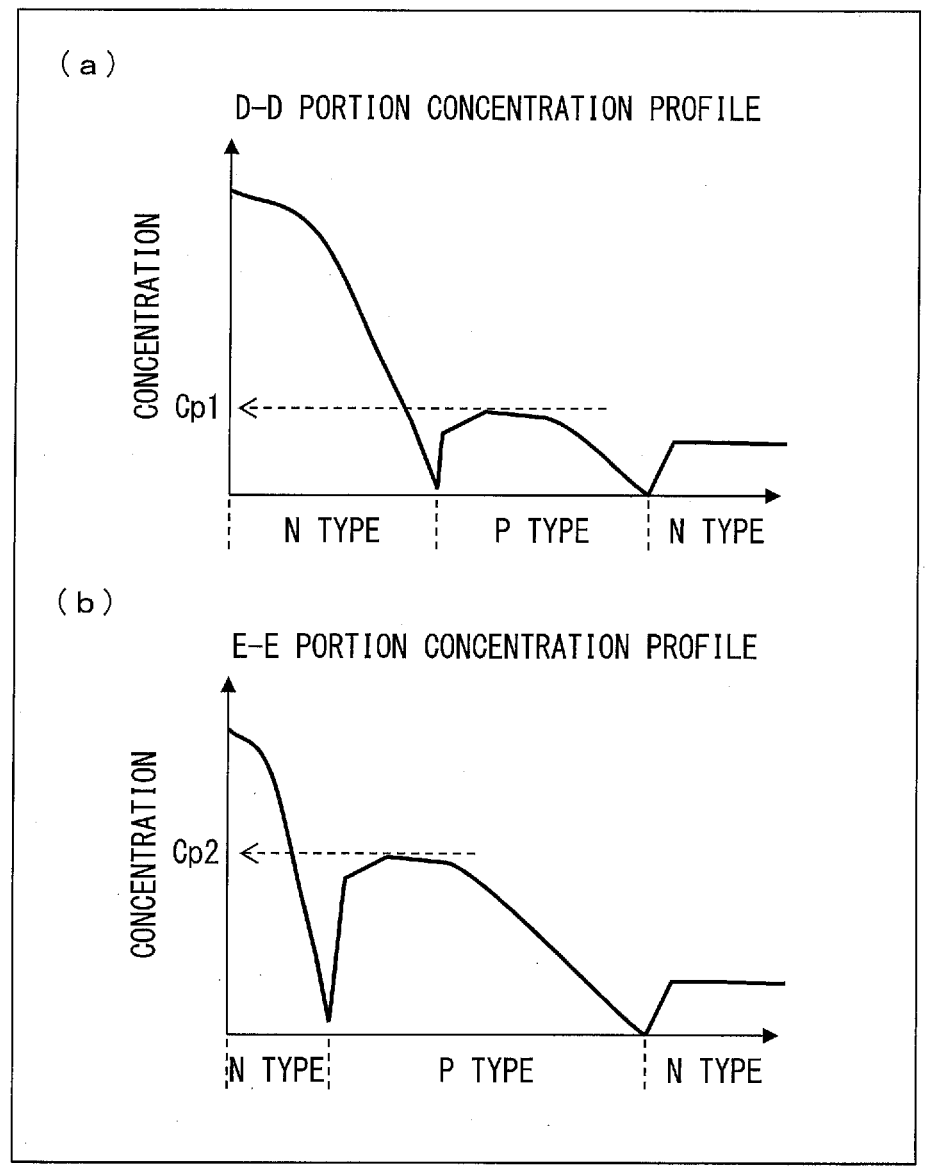

(a) of FIG. 5 is a view illustrating a concentration profile obtained at a D-D portion illustrated in FIG. 4. (b) of FIG. 5 is a view illustrating a concentration profile obtained at an E-E portion illustrated in FIG. 4.

Figure 6:
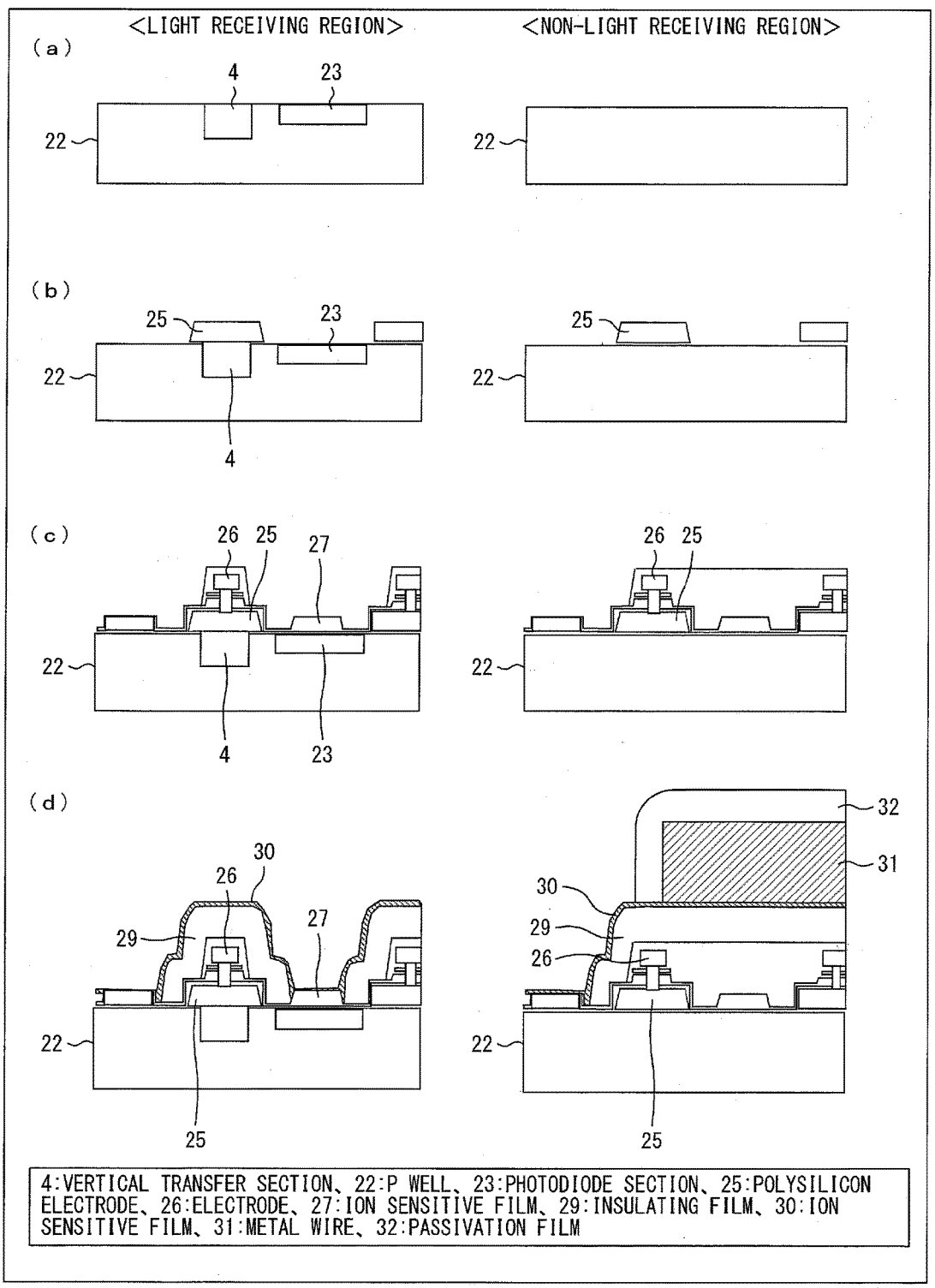

(a) through (d) of FIG. 6 are cross-sectional views each illustrating steps for producing the ion sensor in accordance with Embodiment 2 of the present invention.

Figure 7:
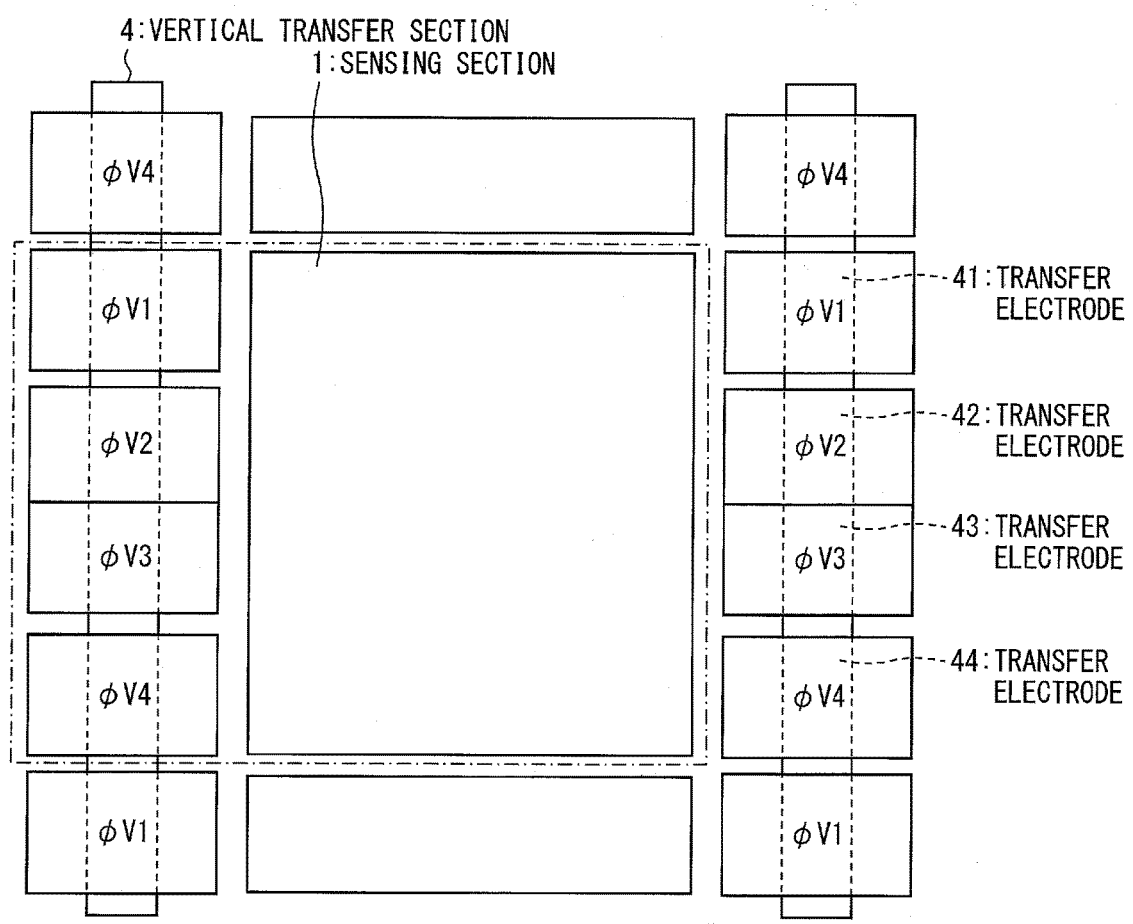

FIG. 7 is a plan view, illustrating a structure of one cell provided in the ion sensor in accordance with Embodiments 1 and 2 which cell includes portions of which a state of an electric potential is illustrated, for explaining operation in accordance with Embodiments 3 and 4 of the present invention.

Figure 8:
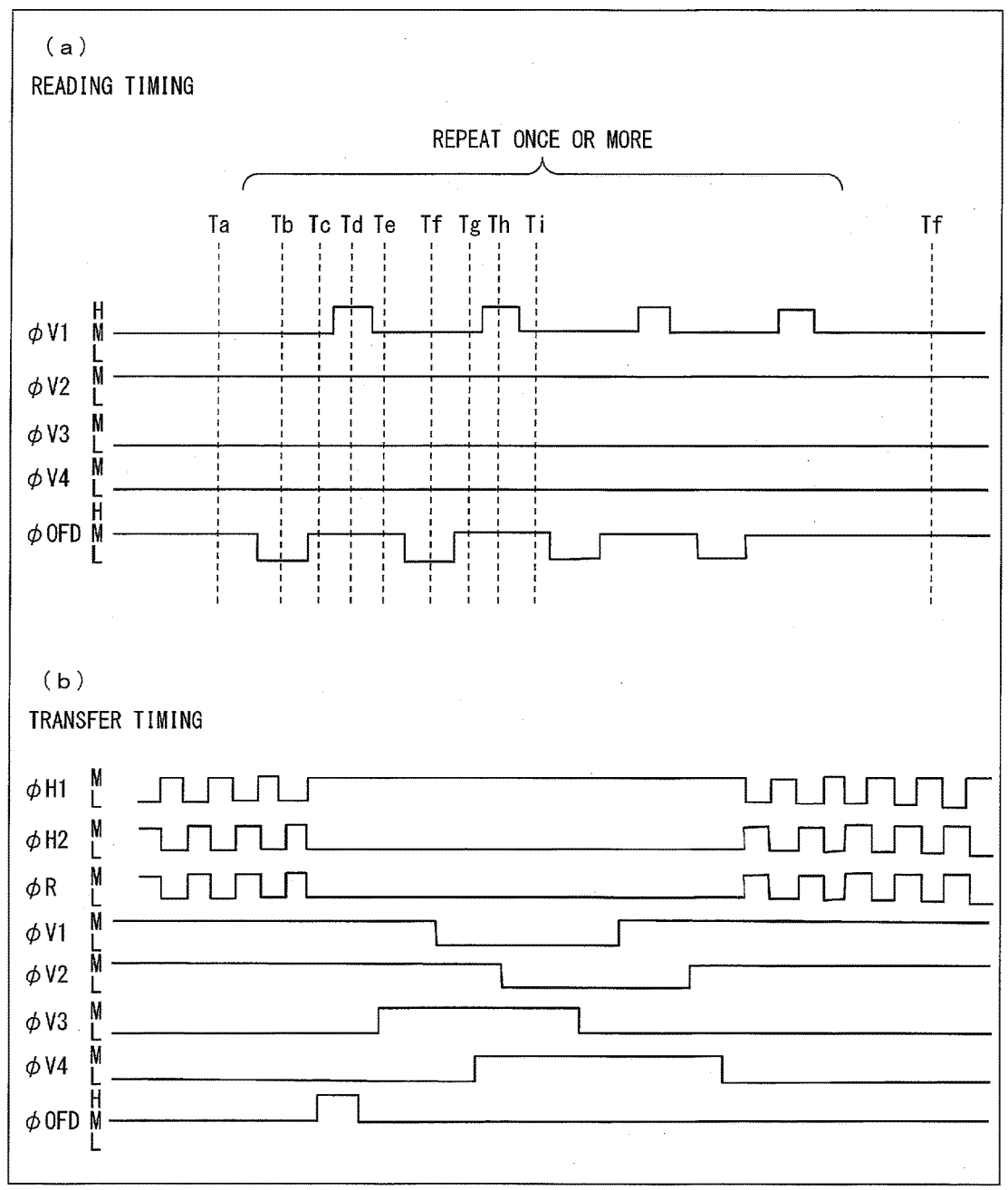

(a) of FIG. 8 is a timing diagram illustrating operation of reading out electric charges which operation is conducted in the ion sensor illustrated in FIG. 7. (b) of FIG. 8 is a timing diagram illustrating operation of transferring electric charges which operation is conducted in the ion sensor illustrated in FIG. 7.

Figure 9:
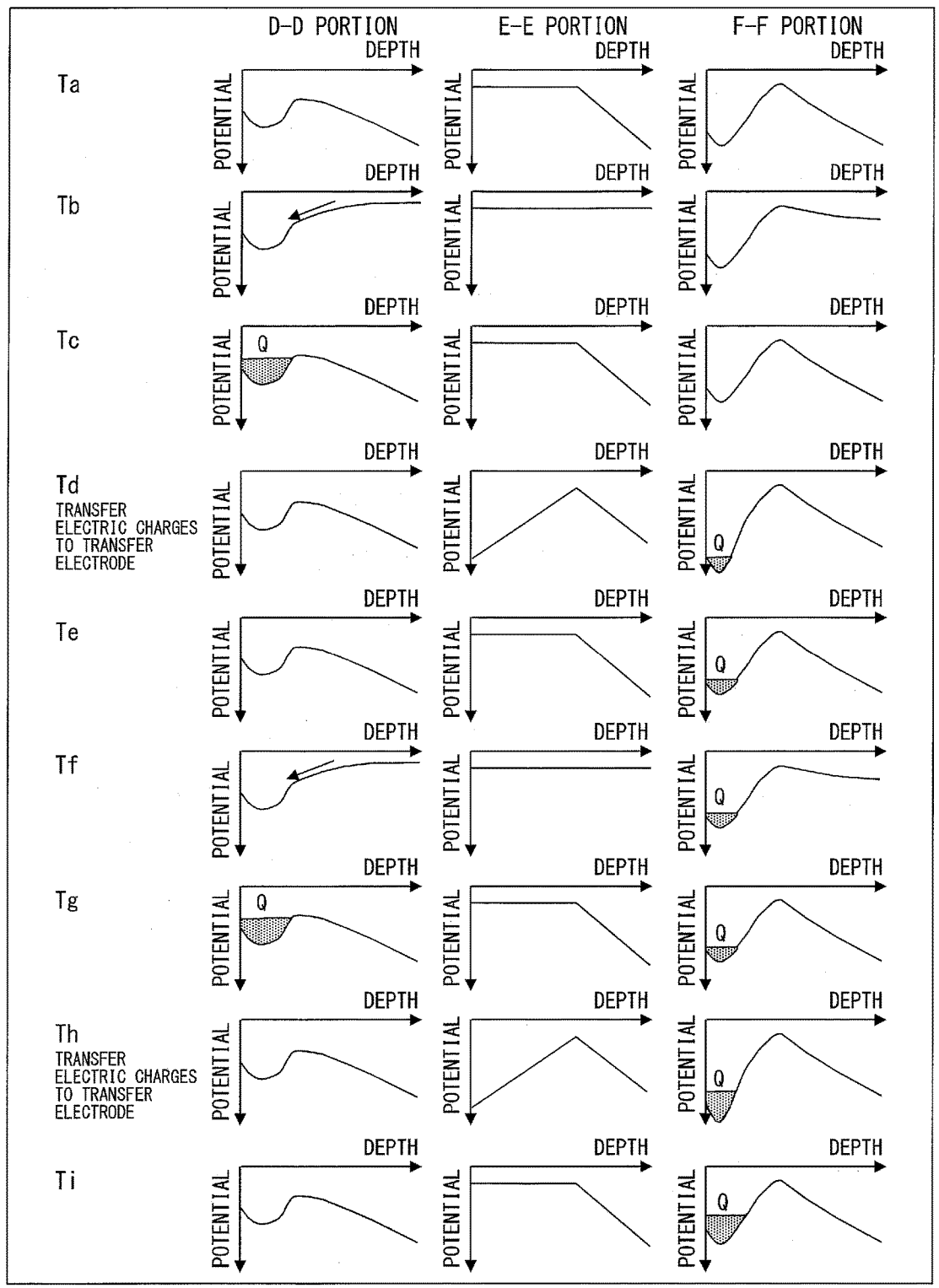

FIG. 9 is a view illustrating changes in state of an electric potential and in state of electric charges at each portion illustrated in FIG. 7.

(a) through (c) of FIG. 10 are views each illustrating a state of an electric potential of and a state of electric charges accumulated in a sensing section illustrated in FIG. 7, each of which states changes depending on whether or not a hydrogen ion is present. (d) of FIG. 10 is a graph illustrating a change in amount of the electric charges with respect to an amount of the hydrogen ion, in the sensing section of the ion sensor in accordance with Embodiments 1 and 2.

DESCRIPTION OF EMBODIMENTS

[Embodiment 1]

The following description will discuss Embodiments 1 of the present invention with reference to FIGS. 1 through 5.

(Configuration of Ion Sensor 100)

(a) of FIG. 1 is an enlarged plan view illustrating part of an ion sensor 100 in accordance with Embodiment 1 of the present invention. (b) of FIG. 1 is a cross-sectional view illustrating the ion sensor 100 taken along a line A-A illustrated in (a) of FIG. 1 and viewed in a direction of arrows shown by the line A-A. (c) of FIG. 1 is a cross-sectional view illustrating the ion sensor 100 taken along a line B-B illustrated in (a) of FIG. 1 and viewed in a direction of arrows shown by the line B-B. (c) of FIG. 1 is also a cross-sectional view illustrating the ion sensor 100 taken along a line C-C illustrated in (a) of FIG. 1 and viewed in a direction of arrows shown by the line C-C. FIG. 2 is a plan view illustrating a configuration of the ion sensor in accordance with Embodiments 1 and 2.

As illustrated in FIG. 2, the ion sensor 100 in accordance with Embodiment 1 includes a light receiving region 5, a non-light receiving region 101, and an optical black 102. The ion sensor 100 is a photodiode-type ion concentration sensor employing a CCD image sensor.

The light receiving region 5 has a quadrangular shape, and is configured such that a plurality of sensing structures are arranged in a matrix manner. The optical black 102 indicates a section where black pixels are provided, and is provided so as to surround the light receiving region 5. The optical black 102 is not used for sensing.

The non-light receiving region 101 is provided so as to surround the optical black 102, and is not involved in light-receiving. The non-light receiving region 101 includes a horizontal transfer section 7 (later described).

As illustrated in (a) of FIG. 1, the ion sensor 100 further includes sensing sections 1, first gate electrodes 2, second gate electrodes 3, vertical transfer sections 4, an adding section 6, a horizontal transfer section 7, an output gate 8, a floating diffusion section 9, a reset gate 10, a reset drain 11, and an output transistor 12. The sensing sections 1, the first gate electrodes 2, the second gate electrodes 3, the vertical transfer sections 4 are provided in the light receiving region 5. The adding section 6, the horizontal transfer section 7, the output gate 8, the floating diffusion section 9, the reset gate 10, the reset drain 11, and the output transistor 12 are provided in the non-light receiving region 101.

Each of the sensing sections 1 is a photoelectric conversion section which converts received light into electric charges. Each of the sensing sections 1 is made up of, for example, a photodiode, and has a diode in which the electric charges obtained by conversion are accumulated.

Each of the first gate electrodes 2 (transfer electrode) is a gate electrode used to control reading of electric charges accumulated in a corresponding one of the sensing sections 1. An ON voltage is applied to the each of the first gate electrodes 2 so that the electric charges are read out. Further, each of the first gate electrodes 2 is an electrode used to control transfer of electric charges, transferred from a side of one of the second gate electrodes 3 which one comes before the each of the first gate electrodes 2, to a side of another one of the second gate electrodes 3 which another one comes after the each of the first gate electrodes 2. Each of the second gate electrodes 3 (transfer electrode) is a gate electrode used to control transfer of electric charges, which have been read out, in a vertical direction. An On voltage is applied to each of the first gate electrodes 2 and the second gate electrodes 3 so that the electric charges are transferred.

Each of the vertical transfer sections 4 (electric charge transfer section) transfers electric charges, which have been read out, in the vertical direction in response to ON voltages applied to respective corresponding ones of the first gate electrodes 2 or ON voltages applied to respective corresponding ones of the second gate electrodes 3. Each of the vertical transfer sections 4 is configured such that a plurality of MOS capacitors are arranged so as to be adjacent to each other.

The adding section 6 is made up of one end parts of the vertical transfer sections 4 which one end parts are connected to each other. The adding section 6 adds electric charges transferred by each of the vertical transfer sections 4 which are ultimately connected to each other.

Each of cells is made up of (i) one of the sensing sections 1, (ii) one of the first gate electrodes 2 which one corresponds to the one of the sensing sections 1, (iii) one of the second gate electrodes 3 which one corresponds to the one of the sensing sections 1, and (iv) part of a corresponding one of the vertical transfer sections 4 which part corresponds to the one of the sensing sections 1.

The horizontal transfer section 7 (electric charge transfer section) has a configuration similar to those of the vertical transfer sections 4, and transfers, in a horizontal direction, electric charges supplied from the adding section 6.

The output gate 8 is a gate circuit for supplying, to the floating diffusion section 9, electric charges transferred from the horizontal transfer section 7. Only in a case where an ON voltage is applied to the output gate 8, the output gate 8 outputs the electric charges.

The floating diffusion section 9 has a capacitor made up of an N-type region. The floating diffusion section 9 is a detecting section (electric charge detecting section) which detects, as a voltage, an amount of electric charges supplied from the output gate 8, by outputting the amount of the electric charges as a voltage corresponding to a capacitance value of the capacitor.

The reset gate 10 is a section for resetting a voltage corresponding to one cell which voltage has been outputted by the floating diffusion section 9, before the floating diffusion section 9 outputs a voltage corresponding to a subsequent cell. The reset drain 11 is a section for applying, to the floating diffusion section 9, the voltage which has been reset by the reset gate 10. The reset gate 10 is in an off-state while the floating diffusion section 9 is detecting electric charges. In contrast, the reset gate 10 is in an on-state while being conducting such reset operation. In this manner, a voltage outputted by the floating diffusion section 9 is reset to a voltage which is to be applied to the reset drain 11.

The output transistor 12 functions as an amplifier having an extremely high input resistance. As such, the output transistor 12 amplifies, while buffering, a voltage outputted from the floating diffusion section 9, and outputs the voltage as a signal voltage.

Note that the output gate 8, the reset gate 10, the floating diffusion section 9, and the output transistor 12 make up an output section. The ion sensor 100 can include one output section at one position. Alternatively, the ion sensor 100 can include a plurality of output sections at a respective plurality of positions.

As illustrated in (b) and (c) of FIG. 1, the ion sensor 100 includes the vertical transfer sections 4, an N-type substrate 21, a P well 22, photodiode sections 23, a protective film 24, electrodes 26, ion sensitive films 27, light-blocking films 28, insulating films 29, and an ion sensitive film 30.

The vertical transfer sections 4 and the photodiode sections 23 are provided, so as to be spaced out, on an upper part of the P well 22 (P-type diffusion region) layered on the N-type substrate 21 (semiconductor substrate). On each of the vertical transfer sections 4, corresponding ones of the first gate electrodes 2 and corresponding ones of the second gate electrodes 3 are provided.

The electrodes 26 are provided on the first gate electrodes 2 so as to be connected with the first gate electrodes 2. The electrodes 26 are connected to a power source line. The light-blocking films 28 are provided on the first gate electrodes 2, the second gate electrodes 3, and the electrodes 26 so as to cover the first gate electrodes 2, the second gate electrodes 3, and the electrodes 26. The vertical transfer sections 4, the adding section 6, the horizontal transfer section 7, the output gate 8, the floating diffusion section 9, the reset gate 10, and the reset drain 11 are provided, as an N-type diffusion layer, on the P well 22, whose type is opposite to that of the N-type substrate 21.

Each of the electrodes 26 is made up of a film made of high-melting metal, such as TiN and W, or its silicide. This allows high-temperature heat treatment. It is therefore possible to suppress an interface state and to suppress noise. Furthermore, the high-melting metal or its silicide has a low resistance. This allows a reduction in delay of a signal. It is therefore possible to realize high-speed operation. Moreover, the high-melting metal or its silicide is a substance having a high light-blocking effect. It is therefore possible to prevent optical noise from entering the N-type substrate 21.

Note that, as with the case of the electrodes 26, an electrode or a wire, other than the electrodes 26, which is included in the ion sensor 100 is preferably made of the foregoing substance.

The light-blocking films 28 are provided on polysilicon electrodes 25 and the electrodes 26 so as to cover the polysilicon electrodes 25 and the electrodes 26. The light-blocking films 28 block light so that the polysilicon electrodes 25 are not affected by the light in a case where a substantial image of a test body is simultaneously required or in a case where measurement needs to be carried out in a bright state. The insulating films 29 are provided on the light-blocking films 28 so as to cover the light-blocking films 28.

On the other hand, the ion sensitive films 27 are provided on the respective sensing sections 1. In a case where the ion sensor 100 is used as a sensor for photoelectric conversion, the ion sensitive films 27 are provided mainly so as to suppress reflection of light on a surface of the N-type substrate 21. Therefore, in a case where (i) the ion sensor 100 is not used as a sensor for photoelectric conversion and (ii) light refection is not necessary to be suppressed, the ion sensitive films 27 can be omitted.

The ion sensitive film 30 is provided on the insulating films 29 and the ion sensitive films 27 so as to cover the insulating films 29 and the ion sensitive films 27. The ion sensitive film 30 has ion sensitivity such that, in a case where the ion sensitive film 30 is in contact with a particular ion, the ion sensitive film 30 changes, depending on an ion concentration, an electric potential, in a vicinity of the ion sensitive film 30, of each of the sensing sections 1. The ion sensitive film 30 also functions as a water-resistant film which prevents water from entering a layer under the ion sensitive film 30.

The protective film 24 is provided on an entire chip including part of the ion sensitive film 30 which part is provided on each of the sensing sections 1. The protective film 24 removes large unevenness, electrically insulates an upper wire (later described) from a lower wire (later described), and facilitates processing of the upper wire.

(Production of Ion Sensor 100)

(a) through (e) of FIG. 3 are cross-sectional view each illustrating steps for producing the ion sensor 100. A left side of FIG. 3 illustrates steps for producing part of the light receiving region 5, while a right side of FIG. 3 illustrates steps for producing part of the non-light receiving region 101. FIG. 4 is a cross-sectional view illustrating a structure of one cell provided in the ion sensor 100. (a) of FIG. 5 is a view illustrating a concentration profile obtained at a D-D portion illustrated in FIG. 4. (b) of FIG. 5 is a view illustrating a concentration profile obtained at an E-E portion illustrated in FIG. 4.

First, in a case of the light receiving region 5, the photodiode sections 23 and the vertical transfer sections 4 are formed, by ion implantation and photolithography, on the P well 22 formed on the N-type substrate 21 (see (a) of FIG. 3). The photodiode sections 23 serve as the respective sensing sections 1.

In a case where electron injection is performed via the N-type substrate 21, an electric potential of the N-type substrate 21 is changed and then the electron injection is performed. Therefore, part of the P well 22 on which part each of the photodiode sections 23 is formed is different, in dopant concentration, from the other part of the P well 22 so that no electric charge is injected into N-type regions (the vertical transfer sections 4, the horizontal transfer section 7, and the like) other than the photodiode sections 23 (sensing sections 1) formed on the P well 22. This difference in dopant concentration varies along a direction perpendicular to an interface between the N-type substrate 21 and the P well 22 (see FIG. 4). In the concentration profile illustrated in (a) of FIG. 5, a left part indicates a sensing section 1 of an N type, a middle part indicates the P well 22 of a P type, and a right part indicates the N-type substrate 21 of an N type. In the concentration profile illustrated in (b) of FIG. 5, a left part indicates a polysilicon electrode 25 of an N type, a middle part indicates the P well 22 of a P type, and a right part indicates the N-type substrate 21 of an N type.

According to the concentration profile obtained at the D-D portion extending through a photodiode section 23 illustrated in FIG. 4, a P-type peak concentration Cp1 of a P-type region (P well 22) is low (see (a) of FIG. 5). This causes electric charges generated in in the N-type substrate 21 to easily move to the sensing section 1. On the other hand, at the E-E portion extending through a vertical transfer section 4 illustrated in FIG. 4, a P-type peal concentration Cp2 is higher, by one digit or more, than the P-type peak concentration Cp1 (see the concentration profile illustrated in (b) of FIG. 5). This causes the electric charges generated in the N-type substrate 21 not to easily move to the vertical transfer section 4.

Next, in the case of the receiving light region 5, the polysilicon electrodes 25 are formed on each of the vertical transfer sections 4 (see (b) of FIG. 3). The polysilicon electrodes 25 serve as the first gate electrodes 2 and the second gate electrodes 3. On the other hand, in the case of the non-light receiving region 101, the polysilicon electrodes 25 are formed on the P well 22.

Then, in the case of the light receiving region 5, the electrodes 26 are formed each of which is to be connected to a corresponding one of the polysilicon electrodes 25 provided in each of the cells. The electrodes 26 are drawn around the ion sensor 100 and connected to the power source line. Further, in order that electric charges can be read out more than once, ion implantation dosage with respect to the photodiode sections 23 and ion implantation dosage with respect to the vertical transfer sections 4 are set so that each of the vertical transfer sections 4 can secure a capacitance that is greater than an amount of electric charges read out more than once from a corresponding one of the photodiode sections 23.

Further, the ion sensitive films 27 each having a film thickness in a range of 1 (one) nm to 100 nm are formed on the respective photodiode sections 23. Note that silicon oxide films can be formed between the ion sensitive films 27 and the photodiode sections 23 so as to further increase electric insulation between the ion sensitive films 27 and the photodiode sections 23.

Here, in general, each of the photodiode sections 23 is arranged such that) $B^+$ is formed shallowly and thickly in a vicinity of a surface of the each of the photodiode sections 23 so as to reduce a dark current which serves as a noise component. Note, however, that, in a case where $B^+$ is too thick, each of the ion sensitive films 27 is decreased in sensitivity to a change in electric potential. In view of this, in Embodiment 1, a desired range of a concentration of $B^+$ in the vicinity of the surface of the each of the photodiodes 23 is between 1E15 ions/$cm^2$ and 8E18 ions/$cm^2$.

On the other hand, also in the case of the non-light receiving region 101, the electrodes 26 are formed on the respective polysilicon electrodes 25

Thereafter, in both the cases of the light receiving region 5 and the non-light receiving region 101, the light-blocking films 28 are formed so as to cover the polysilicon electrodes 25 and the electrodes 26 (see (d) of FIG. 3).

Further, in both the cases of the light receiving region 5 and the non-light receiving region 101, the insulating films 29 are formed on the respective light-blocking films 28, and then the ion sensitive film 30 is formed on an entire region including the ion sensitive films 27 and the insulating films 29 (see (e) of FIG. 3).

The film thickness of each of the ion sensitive films 27 and a film thickness of the ion sensitive film 30 are not limited to the foregoing film thickness, provided that each of the ion sensitive films 27 and 30 has (i) a number of dangling bonds to each of which an ion adheres and (ii) a film quality and a film thickness each of which does not allow the ion to permeate the each of the ion sensitive films 27 and 30. The ion sensitive films 27 and 30 are made of, for example, silicon nitrides. Other examples of the ion sensitive films 27 and 30 encompass an aluminum oxide film and a tantalum oxide film. However, in a case where the each of the ion sensitive films 27 and 30 is thin, this causes a considerable change in electric potential of the N-type substrate 21. This results in an improvement in sensitivity. Therefore, the each of the ion sensitive films 27 and 30 is preferably thin. Out of the silicon nitrides, LP-SiN (Low Pressure Chemical Vapor Deposition Silicon Nitride) is preferably used.

In the case of the non-light receiving region 101, after an aluminum wire is formed as a metal wire 31, a passivation film 32 is formed so as to cover the metal wire 31. Thereafter, in both the cases of the light receiving region 5 and the non-light receiving region 101, the protective film 24 is removed with use of an agent so as to expose the ion sensitive film 30 provided on the photodiode sections 23. The protective film 24 is provided for the purpose of evening a base so as to facilitate processing of an aluminum wire (not illustrated). Therefore, before the aluminum wire is formed, the protective film 24 is formed on the entire chip so as to even the base, and then the aluminum wire is processed. However, in a case where the protective film 24 is remained, the ion sensitive films 27 are embedded in the protective film 24. Therefore, after the aluminum wire is formed, it is necessary to remove the protective film 24 so as to expose the ion sensitive film 30.

[Embodiment 2]

The following description will discuss Embodiment 2 of the present invention with reference to FIGS. 2 and 6. Note that, in Embodiment 2, identical reference signs will be given, for convenience, to respective components having functions identical to those of the components described in Embodiment 1, and descriptions of the components will be omitted.

(Configuration of Ion Sensor 100A)

As illustrated in FIG. 2, an ion sensor 100A in accordance with Embodiment 2 also includes a light receiving region 5, a non-light receiving region 101, and an optical black 102, as with the case of the ion sensor 100 of Embodiment 1. Note, however, that, unlike the ion sensor 100, the ion sensor 100A does not include a light-blocking film 28 described in Embodiment 1. In a case where measurement is carried out in a dark state, it is not necessary to block light. Therefore, in a case where such a use situation is assumed, no light-blocking film 28 is required.

(Production of Ion Sensor 100A)

(a) through (d) of FIG. 6 are cross-sectional views each illustrating steps for producing the ion sensor 100A. A left side of FIG. 6 illustrates steps for producing part of the light receiving region 5, while a right side of FIG. 6 illustrates steps for producing part of the non-light receiving region 101. In (a) through (d) of FIG. 6, an N-type substrate 21 is not illustrated for convenience. Further, in (d) of FIG. 6, a protective film 24 is not illustrated.

The steps illustrated in (a) through (c) of FIG. 6 are identical to the respective steps illustrated in (a) through (c) of FIG. 3. Therefore, descriptions of the steps illustrated in (a) through (c) of FIG. 6 will be omitted here. In the step illustrated in (d) of FIG. 6, a process identical to that in the step illustrated in (e) of FIG. 3 is carried out, except that no light-blocking film 28 is formed.

[Embodiment 3]

The following description will discuss Embodiment 3 of the present invention with reference to FIGS. 1, 4, and 7 through 10. Embodiment 3 will describe how an ion sensor 100, 100A operates and detects an ion concentration. Note that, in Embodiment 3, identical reference signs will be given, for convenience, to respective components having functions identical to those of the components described in Embodiments 1 and 2, and descriptions of the components will be omitted.

FIG. 7 is a plan view illustrating a structure of one cell provided in the ion sensor 100, 100A. (a) of FIG. 8 is a timing diagram illustrating operation of reading out electric charges which operation is conducted in the ion sensor 100, 100A. (b) of FIG. 8 is a timing diagram illustrating operation of transferring electric charges which operation is conducted in the ion sensor 100, 100A. FIG. 9 is a view illustrating changes in state of an electric potential and in state of electric charges at each portion of the ion sensor 100, 100A. (a) through (c) of FIG. 10 are views each illustrating a state of an electric potential and a state of electric charges at a specific portion of the ion sensor 100, 100A, each of which states changes depending on whether or not a hydrogen ion is present. (d) of FIG. 10 is a graph illustrating a change in amount of the electric charges with respect to an amount of the hydrogen ion, in a sensing section 1 of the ion sensor 100, 100A.

(Basic Operation)

As illustrated in (a) and (b) of FIG. 1, by applying an ON voltage to a corresponding one of first gate electrodes 2, electric charges accumulated in each of sensing sections 1 provided in respective cells are read out to one of vertical transfer sections 4 which one is adjacent to the each of the sensing sections 1. Next, as illustrated in (c) of FIG. 1, by applying an ON voltage to a corresponding one of second gate electrodes 3, the electric charges accumulated in part of the one of the vertical transfer sections 4, which part is located under the corresponding one of the first gate electrodes 2, is transferred to another part of the one of the vertical transfer sections 4 which another part is located under the corresponding one of the second gate electrodes 3. Repetition of such operation causes the electric charges to be transferred to the horizontal transfer section 7.

As with the case of the vertical transfer sections 4, a horizontal transfer section 7 transfers the electric charges via another gate electrode (not illustrated). An amount of the electric charges is ultimately detected and then outputted as a voltage by an output section made up of an output gate 8, a reset gate 10, a floating diffusion section 9, and an output transistor 12.

The above operation can be arranged such that (i) electric charges are read out more than once from each of the sensing sections 1 provided in the respective cells to a corresponding one of the vertical transfer sections 4 and (ii) after the electric charges thus read out are accumulated in the corresponding one of the vertical transfer sections 4, the electric charges are vertically transferred (step (a)). This allows an improvement in S/N of an outputted voltage.

(Details of Reading Out and Transferring Charge)

Operation of reading out and transferring electric charges will be described below with reference to a structure in which, instead of a first gate electrode 2 and a second gate electrode 3, transfer electrodes 41 through 44 are provided in one cell (in FIG. 7, part enclosed by an alternate long and short dash line), that is, with respect to one sensing section 1 as illustrated in FIG. 7. Each of the transfer electrodes 41 through 44 is an electrode that is formed as a polysilicon electrode 25 (see FIG. 3), as with the case of the first gate electrode 2 and the second gate electrode 3. The transfer electrodes 41 through 44 are arranged on a vertical transfer section 4 so as to line up. A drive pulse $\varphi V1$ is applied to the transfer electrode 41 which is used to read out electric charges from the cell. Drive pulses $\varphi V2$ through $\varphi V4$ are applied to the respective transfer electrodes 42 through 44 each of which is used to transfer the electric charges.

The operation of reading out electric charges will be described below with reference to (a) of FIG. 8 and FIG. 9. In FIG. 9, "depth" added to each horizontal axis of graphs indicates a distance from a surface of the cell and, a right end of the each horizontal axis indicates a distance from the surface of the cell to an N-type substrate 21. In FIG. 9, left ones of the graphs each illustrate a state of an electric potential and a state of electric charges which states are observed at a D-D portion extending through a photodiode section 23 as illustrated in FIG. 4. Meddle ones of the graphs each illustrate the state of the electric potential and the state of the electric charges which states are observed at an E-E portion extending through the polysilicon electrode 25 as illustrated in FIG. 4. Meanwhile, in FIG. 9, right ones of the graphs each illustrate the state of the electric potential and the state of the electric charges which states are observed at an F-F portion extending through a region between the photodiode section 23 and the vertical transfer section 4 as illustrated in FIG. 4.

First, as illustrated in (a) of FIG. 8, a timing Ta indicates an initial state. Upon a shift to a timing Tb, a voltage $\varphi OFD$ (a voltage of approximately 0 (zero) V to 3 V) is applied to the N-type substrate 21. This causes electric charges Q, which varies depending on an initial electric potential, to start to be accumulated in the sensing section 1 (see an arrow illustrated in FIG. 9).

At a subsequent timing Tc, application of the voltage φOFD to the N-type substrate 21 is stopped. In this state, as illustrated in FIG. 9, the electric charges Q in a predetermined amount are accumulated in the sensing section 1. Thereafter, at a timing Td, the drive pulse φV1 is applied to the transfer electrode 41. This causes a barrier between the sensing section 1 and the vertical transfer section 4 to be lowered, thereby causing the electric charges Q to be read out from the sensing section 1 to the vertical transfer section 4 (that is, the electric charges Q move from the sensing section 1 to the vertical transfer section 4). At a timing Te, application of the drive pulse φV1 is stopped. Accordingly, the barrier between the sensing section 1 and the vertical transfer section 4 is raised.

At a subsequent timing Tf, the voltage φOFD is again applied to the N-type substrate 21, and electric charges Q accordingly start to be accumulated in the sensing section 1. At a subsequent timing Tg, application of the voltage φOFD to the N-type substrate 21 is stopped. In this state, as illustrated in FIG. 9, the electric charges Q in a predetermined amount are accumulated in the sensing section 1. Thereafter, at a timing Th, the drive pulse φV1 is applied to the transfer electrode 41. This causes the barrier between the sensing section 1 and the vertical transfer section 4 to be lowered, thereby causing the electric charges Q to be read out from the sensing section 1 to the vertical transfer section 4. At a timing Ti, application of the drive pulse φV1 is stopped. Accordingly, the barrier between the sensing section 1 and the vertical transfer section 4 is raised. In this state, the electric charges Q accumulated at the timing Te and the electric charges Q further read out at the timing Th are added and accumulated in the vertical transfer section 4.

Next, the operation of transferring electric charges will be described below with reference (b) of FIG. 8. In (b) of FIG. 8, φH1 and φH2 each represent a drive pulse applied to the horizontal transfer section 7, and φR represents a reset pulse applied to the reset gate 10. The horizontal transfer section 7 includes two adjacent transfer electrodes (not illustrated). The drive pulse φH1 is applied to one of the two adjacent transfer electrodes, whereas the drive pulse φH2 is applied to the other one of the two adjacent transfer electrodes.

First, the voltage φOFD is applied to the N-type substrate 21, and then application of the voltage φOFD is stopped. This causes each of the drive pulses φV1 through φV4 to change between an ON state and an OFF state, thereby causing electric charges to be transferred. Specifically, the electric charges are transferred by the vertical transfer section 4 through (i) a first period in which the drive pulses φV1 and φV2 are each in the ON state (M) and the drive pulses φV3 and φV4 are each in the OFF state (L), (ii) a second period in which the drive pulses φV1 through φV3 are each in the ON state and the drive pulse φV4 is in the OFF state, (iii) a third period in which the drive pulses φV2 and φV3 are each in the ON state and the drive pulses φV1 and φV4 are each in the OFF state, and (iv) a fourth period in which the drive pulses φV1 and φV2 are each in the ON state and the drive pulses φV3 and φV4 are each in the OFF state. This vertical transfer operation is identical to that carried out in a conventional CCD.

On the other hand, in the horizontal transfer section 7, the drive pulses φH1 and φH2 alternately get into an ON state and an OFF state repeatedly. This causes a change in electric potential difference between the transfer electrodes to which the respective drive pulses φH1 and φH2 are applied, thereby causing the electric charges to be transferred. This horizontal transfer operation is also identical to the vertical transfer operation carried out in a conventional CCD.

(Accumulation of Electric Charges Depending on Ion Content)

In a case where a concentration of $H^+$ in a test body is detected, the ion sensor 100, 100A detects an amount of $H^+$ which amount varies depending on a pH in the test body. As the amount of $H^+$ is increased, an electric potential of the sensing section 1 becomes deeper, and an amount of electric charges to be accumulated in the sensing section 1 is increased in proportion to a depth of the electric potential of the sensing section 1. In view of this, an amount of electric charges accumulated in the sensing section 1 in an initial state is first stored, and a difference $\Delta V$, between (i) the amount of the electric charges in the initial state thus stored and (ii) a detected amount of electric charges, is calculated. The difference $\Delta V$ corresponds to $\Delta pH$. It is therefore possible to detect a pH. Storage of the amount of the electric charges accumulated in the sensing section 1 in the initial state and calculation of the difference $\Delta V$ are carried out by, for example, a processing section provided in a detecting device included in the ion sensor 100, 100A. Accumulation of electric charges depending on an amount of an ion will be described below.

In the initial state where there is no $H^+$ on a surface of an ion sensitive film 30 provided on the sensing section 1, electric charges Q are accumulated, in an initial amount, in the sensing section 1 (see (a) of FIG. 10). An amount of the electric charges Q accumulated in the initial state is measured by the forgoing procedure illustrated in FIGS. 8 and 9, and a voltage thus obtained (initial voltage) is stored (step (b)).

Next, in a case where a little amount of $H^+$ comes into contact with the surface of the ion sensitive film 30 provided on the sensing section 1 (detection state), this causes a change in electric potential in a vicinity of a surface of the sensing section 1 due to an effect of $H^+$. The electric potential of the sensing section 1 thus becomes deeper (see (b) of FIG. 10). In this state, in a case where electric charges are injected by applying a voltage to the N-type substrate 21, an increased amount of the electric charges are accumulated in the sensing section 1. The increased amount of the electric charges is measured by the foregoing procedure (step (b)).

In a case where an increased amount of $H^+$ comes into contact with the ion sensitive film 30 provided on the sensing section 1, this causes a further change in electric potential in the vicinity of the surface of the sensing section 1. The electric potential of the sensing section 1 thus becomes much deeper. In this state, in a case where electric charges are injected by applying a voltage to the N-type substrate 21, a further increased amount of the electric charges are accumulated in the sensing section 1. The further increased amount of the electric charges is measured by the foregoing procedure (step (c)).

In either case of (b) and (c) of FIG. 10, as illustrated in (d) of FIG. 10, it is possible to measure, as an ion concentration, the amount of $H^+$ ($\Delta pH$) by calculating the difference $\Delta V$ between (i) a voltage which corresponds to an measured amount of the electric charges (detected voltage) and (ii) a voltage (initial voltage) which is stored and which corresponds to the amount of the electric charges in the initial state (initial value) (step (d)).

(Effect of Embodiment 3)

In Embodiment 3, on the basis of a structure of an image sensor which has highly integrated cells each having a size of not more than 10 μm, the dopant concentration at each part of the P well 22 is optimized so that, in a case where a voltage is applied to the N-type substrate 21, electric charges are injected merely into the sensing section 1. This makes it unnecessary to newly provide an electrode, for electric charge injection, in a vicinity of a surface of the ion sensor. It is therefore possible to increase an area of the sensing section 1 and possible to detect a slight change in electric potential of the sensing section 1. Furthermore, the ion sensor 100, 100A is covered with a protective film 24 so that at least part of the ion sensitive film 30 which part is provided on each of the sensing sections 1 is exposed. This makes it possible to provide a structure in which a wire section and the like, other than a region with which an ion is in contact, have chemical resistance.

According to Embodiment 3, it is possible to provide a highly accurate two-dimensional ion sensor having resolution of not more than 10 μm. This allows a finding to be obtained in regard to a local activity or property in a fine cell such as an iPS (induced Pluripotent Stem) cell. It is currently said that, out of three billion human DNAs, five hundred million are related to diseases. According to Embodiment 3, it is possible to simultaneously carry out measurement with use of two million cells of a chip having a size of approximately 7 mm, and possible to finish an analysis of a base sequence in a short time period.

Moreover, a capacitance of the sensing section can be measured without use of an electric charge supplying section or an electric charge injection adjusting section. It is therefore possible to form finer cells.

In Embodiment 3, electric charges are injected into the sensing section 1 by applying a voltage to the N-type substrate 21. Note, however, that, in a case where the ion sensor 100. 100A is not used as an image sensor, the sensing section 1 does not need to have a photoelectric conversion function. In this case, it is only necessary that the sensing section 1 can accumulate therein electric charges.

[Embodiment 4]

The following description will discuss Embodiment 4 of the present invention with reference to FIGS. 1 and 7 through 10. Note that, in Embodiment 4, identical reference signs will be given, for convenience, to respective components having functions identical to those of the components described in Embodiments 1 through 3, and descriptions of the components will be omitted Embodiments 1 through 3 have described a configuration in which a voltage is applied to the N-type substrate 21 so that electric charges are injected to the sensing section 1. Embodiment 4 will describe, on the other hand, a configuration in which a sensing section 1 is irradiated with light so that electric charges are accumulated in the sensing section 1.

According to the configuration illustrated in (a) through (c) of FIG. 1, the sensing section 1 is made up of a photodiode. With this, by irradiating the sensing section 1 with light, it is possible to cause the sensing section 1 to generate electric charges. Then, as with the case of injecting electric charges via an N-type substrate 21 as illustrated in FIG. 9, it is possible to accumulate, in the sensing section 1, the electric charges thus generated. Irradiation of the sensing section 1 with light is carried out with use of light in a given amount, such as light from an LED, at timings Tc and Tg illustrated in (a) of FIG. 8.

As with the case of Embodiment 3, the electric charges thus accumulated are read out by the configuration illustrated in FIG. 7, and then transferred at timings illustrated in (a) and (b) of FIG. 8. The electric charges thus transferred are detected as illustrated in (d) of FIG. 10.

In Embodiment 4, since electric charges are accumulated in the sensing section 1 by light irradiation, it is not necessary to provide, in each cell, means for injecting electric charges, as with the case of Embodiment 3. It is therefore possible to increase an area of the sensing section 1. Furthermore, it is possible to provide a structure in which a wire section and the like, other than a region with which an ion is in contact, have chemical resistance due to a protective film 24.

[Summary]

An ion concentration sensor in accordance with Aspect 1 of the present invention is an ion concentration sensor including: a semiconductor substrate (N-type substrate 21); a sensing section 1 in which electric charges, used to detect an ion concentration, is accumulated; an electric charge transfer section (vertical transfer section 4, horizontal transfer section 7) which transfers the electric charges accumulated in the sensing section 1; an electric charge detecting section (floating diffusion section 9) which detects an amount of the electric charges that have been transferred; and an ion sensitive film 30 which changes, depending on the ion concentration, the amount of the electric charges to be accumulated in the sensing section 1, the sensing section 1, the electric charge transfer section, and the electric charge detecting section being provided on a diffusion region (P well 22), on the semiconductor substrate, whose type is opposite to that of the semiconductor substrate, part of the diffusion region on which part the sensing section 1 is provided being different, in dopant concentration, from the other part of the diffusion region so that the electric charges are injected merely to the sensing section 1 in a state where a voltage is applied to the semiconductor substrate.

According to the above configuration, in a case where a voltage is applied to the semiconductor substrate, electric charges are injected merely into the sensing section 1. As such, in a case where an ion comes into contact with the ion sensitive film 30, this causes, depending on an ion concentration, a change in amount of electric charges to be accumulated in the sensing section 1. By the electric charge detecting section detecting the amount of the electric charges accumulated in the sensing section 1, it is possible to detect the ion concentration. Since electric charges are thus injected by applying a voltage to the semiconductor substrate, it is not necessary to provide, in a vicinity of a surface of the sensor, an electrode and the like for supplying the electric charges to the sensing section 1. Therefore, it is possible to increase an area of the sensing section in the ion concentration sensor.

An ion concentration sensor in accordance with Aspect 2 of the present invention is an ion concentration sensor including: a sensing section 1 in which electric charges, used to detect an ion concentration of a test body, is accumulated; an electric charge transfer section (vertical transfer section 4, horizontal transfer section 7) which transfers the electric charges accumulated in the sensing section 1; an electric charge detecting section (floating diffusion section 9) which detects an amount of the electric charges that have been transferred; and an ion sensitive film 30 which changes, depending on the ion concentration, the amount of the electric charges to be accumulated in the sensing section, the sensing section 1 generating the electric charges by photoelectric conversion.

According to the above configuration, the sensing section 1 converts light, with which the sensing section 1 is irradiated, into electricity, thereby generating electric charges. As such, in a case where an ion comes into contact with the ion sensitive film 30, this causes, depending on an ion concentration, a change in amount of electric charges to be accumulated in the sensing section 1. By the electric charge detecting section detecting the amount of the electric charges accumulated in the sensing section 1, it is possible to detect the ion concentration. Since electric charges are thus injected by applying a voltage to the semiconductor substrate, it is not necessary to provide, in a vicinity of a surface of the sensor, an electrode and the like for supplying the electric charges to the sensing section 1. Therefore, it is possible to increase an area of the sensing section in the ion concentration sensor.

According Aspect 3 of the present invention, the ion concentration sensor of Aspect 1 or 2 can be arranged such that the ion sensitive film 30 changes, depending on the ion concentration, a depth of an electric potential of the sensing section 1.

According to the above configuration, since a depth of an electric potential of the sensing section 1 is changed depending on an ion concentration, electric charges in an amount corresponding to the ion concentration are accumulated in the sensing section 1.

According to Aspect 4 of the present invention, the ion concentration sensor any one of Aspects 1 through 3 can be arranged so as to further include a transfer electrode (first gate electrode 2, second gate electrode 3) used to control transfer of the electric charges which transfer is carried out by the electric charge transfer section, at least the transfer electrode and a wire connected to the transfer electrode being made up of a film made of high-melting metal or its silicide.

According to the above configuration, it is possible to carry out high-temperature heat treatment. It is therefore possible to suppress an interface state and to suppress noise. Furthermore, the high-melting metal or its silicide has a low resistance. This allows a reduction in delay of a signal. It is therefore possible to realize high-speed operation. Moreover, the high-melting metal or its silicide is a substance having a high light-blocking effect. It is therefore possible to prevent optical noise from entering the N-type substrate 21.

According to Aspect 5 of the present invention, the ion concentration sensor any one of Aspects 1 through 4 can be arranged so as to further include: a protective film which covers the ion concentration sensor, the protective film being provided so that at least part of the ion sensitive film 30 which part is provided on the sensing section 1 is exposed.

According to the above configuration, it is possible to provide a structure in which a wire section and the like, other than a region with which an ion is in contact, have chemical resistance.

A method of detecting an ion concentration in accordance with Aspect 6 of the present invention is a method of detecting an ion concentration with use of an ion concentration sensor recited in any one of Aspects 1 through 5, the electric charge transfer section including: a vertical transfer section 4 which reads out electric charges accumulated in the sensing section 1 and transfers the electric charges in a vertical direction; and a horizontal transfer section 7 which transfers, to the electric charge detecting section, the electric charges that have been transferred from the vertical transfer section 4, the method including the steps of: (a) transferring, to the horizontal transfer section 7, the electric charges which are accumulated in the vertical transfer section 4 by being read out more than once from the sensing section 1 to the vertical transfer section 4, the step (a) being carried out by the vertical transfer section 4; (b) detecting an initial voltage which corresponds to an amount of the electric charges accumulated in an initial state where no ion is in contact with the ion sensitive film 30, the step (b) being carried out by the electric charge detecting section; (c) detecting a detected voltage which corresponds to the amount of the electric charges accumulated in a detection state where an ion is in contact with the ion sensitive film 30, the step (c) being carried out by the electric charge detecting section; and (d) calculating a difference between the detected voltage and the initial voltage.

According to the above configuration, a difference between an initial voltage obtained in the step (b) and a detected voltage obtained in the step (c) is obtained in the step (d). It is possible to detect the difference as an ion concentration. Furthermore, in the step (a), electric charges, which are accumulated in the vertical transfer section 4 by being read out more than once to the vertical transfer section 4, are transferred. It is therefore possible to transfer a large amount of electric charges to the electric charge detecting section. This allows an improvement in S/N of a detected voltage outputted from the electric charge detecting section.

The present invention is not limited to the embodiments, but can be altered by a skilled person in the art within the scope of the claims. An embodiment derived from a proper combination of technical means each disclosed in a different embodiment is also encompassed in the technical scope of the present invention. Further, it is possible to form a new technical feature by combining the technical means disclosed in the respective embodiments.

INDUSTRIAL APPLICABILITY

The present invention can be suitably used for analysis of a DNA base sequence, analysis, classification, or discrimination of a property of a cell such as an iPS cell, or determination of an influenza virus.

REFERENCE SIGNS LIST

1 Sensing section
4 Vertical transfer section (electric charge transfer section)
7 Horizontal transfer section (electric charge transfer section)
9 Floating diffusion section (electric charge detecting section)
21 N-type substrate (semiconductor substrate)
22 P well (diffusion region)
23 Photodiode section (sensing section)
24 Protective film
30 Ion sensitive film
100 Ion sensor (ion concentration sensor)
100A Ion sensor (ion concentration sensor)

The invention claimed is:
1. An ion concentration sensor comprising:
a semiconductor substrate;
a sensing section in which electric charges, used to detect an ion concentration, is accumulated;
an electric charge transfer section which transfers the electric charges accumulated in the sensing section;
an electric charge detecting section which detects an amount of the electric charges that have been transferred; and
an ion sensitive film which changes, depending on the ion concentration, the amount of the electric charges to be accumulated in the sensing section,
the sensing section, the electric charge transfer section, and the electric charge detecting section being provided on a diffusion region, on the semiconductor substrate, whose type is opposite to that of the semiconductor substrate, part of the diffusion region on which part the sensing section is provided being different, in dopant concentration, from the other part of the diffusion region so that the electric charges are injected merely to the sensing section in a state where a voltage is applied to the semiconductor substrate.

2. The ion concentration sensor as set forth in claim 1, wherein the ion sensitive film changes, depending on the ion concentration, a depth of an electric potential of the sensing section.

3. The ion concentration sensor as set forth in claim 1, further comprising:

a protective film which covers the ion concentration sensor, the protective film being provided so that at least part of the ion sensitive film which part is provided on the sensing section is exposed.

4. A method of detecting an ion concentration with use of an ion concentration sensor recited in claim 1, the electric charge transfer section including:

a vertical transfer section which reads out electric charges accumulated in the sensing section and transfers the electric charges in a vertical direction; and a horizontal transfer section which transfers, to the electric charge detecting section, the electric charges that have been transferred from the vertical transfer section, the method comprising the steps of:

(a) transferring, to the horizontal transfer section, the electric charges which are accumulated in the vertical transfer section by being read out more than once from the sensing section to the vertical transfer section, the step (a) being carried out by the vertical transfer section;

(b) detecting an initial voltage which corresponds to an amount of the electric charges accumulated in an initial state where no ion is in contact with the ion sensitive film, the step (b) being carried out by the electric charge detecting section;

(c) detecting a detected voltage which corresponds to the amount of the electric charges accumulated in a detection state where an ion is in contact with the ion sensitive film, the step (c) being carried out by the electric charge detecting section; and (d) calculating a difference between the detected voltage and the initial voltage.

* * * * *

UNITED STATES PATENT AND TRADEMARK OFFICE
CERTIFICATE OF CORRECTION

PATENT NO. : 10,031,101 B2
APPLICATION NO. : 14/885240
DATED : July 24, 2018
INVENTOR(S) : Satoshi Saitoh et al.

It is certified that error appears in the above-identified patent and that said Letters Patent is hereby corrected as shown below:

On the Title Page

Item (73), Assignees, should read as follows:
-- SHARP KABUSHIKI KAISHA, Sakai (JP); NATIONAL UNIVERSITY CORPORATION TOYOHASHI UNIVERSITY OF TECHNOLOGY, Aichi (JP) --

Signed and Sealed this
Twenty-sixth Day of April, 2022

Katherine Kelly Vidal
*Director of the United States Patent and Trademark Office*